(12) United States Patent
Sasajima et al.

(10) Patent No.: US 9,153,418 B2
(45) Date of Patent: Oct. 6, 2015

(54) CHARGED PARTICLE RADIATION APPARATUS

(71) Applicant: Hitachi High-Technologies Corporation, Minato-ku, Tokyo (JP)

(72) Inventors: Fumihiro Sasajima, Tokyo (JP); Yoshihiro Kimura, Tokyo (JP); Akihiro Miura, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 14/461,051

(22) Filed: Aug. 15, 2014

(65) Prior Publication Data

US 2015/0076349 A1    Mar. 19, 2015

(30) Foreign Application Priority Data

Sep. 13, 2013 (JP) ................. 2013-189987

(51) Int. Cl.
*H01J 37/26* (2006.01)
*G21K 5/04* (2006.01)
*G01N 23/225* (2006.01)
*H01J 37/244* (2006.01)
*H01J 37/29* (2006.01)

(52) U.S. Cl.
CPC .......... *H01J 37/265* (2013.01); *G01N 23/2251* (2013.01); *H01J 37/244* (2013.01); *H01J 37/292* (2013.01)

(58) Field of Classification Search
USPC ............ 250/306, 307, 309, 310, 311, 396 R, 250/397, 398, 492.1, 492.3
See application file for complete search history.

(56) References Cited

U.S. PATENT DOCUMENTS

| 6,005,247 | A  | * | 12/1999 | Baum ........................... 250/310 |
| 7,977,632 | B2 |   | 7/2011  | Todokoro et al. |
| 8,384,030 | B2 |   | 2/2013  | Ueda et al. |
| 2004/0222806 | A1 | * | 11/2004 | Yamada ........................ 324/751 |
| 2009/0268184 | A1 | * | 10/2009 | Lin et al. ......................... 355/67 |

FOREIGN PATENT DOCUMENTS

WO    WO 2013/011792 A1    1/2013

* cited by examiner

*Primary Examiner* — Nicole Ippolito
(74) *Attorney, Agent, or Firm* — Miles & Stockbridge P.C.

(57) ABSTRACT

A charged particle radiation apparatus includes a control device that switches between a first charged particle beam and a second charged particle beam, the first charged particle beam being scanned to acquire an image and a waveform signal, the second charged particle beam being scanned over a sample before the scan of the first charged particle beam and used to charge the sample more than the first charged particle beam; wherein the control device is configured to acquire at least one of signal waveform data and image data about a pattern formed on the sample in accordance with a scan performed on the sample by the second charged particle beam, and to stop, when the acquired data has proved to be indicative of a predetermined state, the scan of the second charged particle beam.

6 Claims, 10 Drawing Sheets

FIG. 2

(1) INITIAL STAGE OF PRE-DOSING:
CENTRAL PORTION OF IMAGE HAS HIGH LUMINANCE AND LOOKS WHITISH. HIGH-LUMINANCE PORTION ENLARGES TOWARD EDGE OF SCREEN.

(2) FIRST INTERMEDIATE STAGE OF PRE-DOSING:
HIGH-LUMINANCE PORTION GENERATED DURING PRE-DOSING ENLARGES TOWARD VICINITY OF EDGE OF SCREEN (AND PARTIALLY ENLARGES BEYOND SIZE OF SCREEN.

(3) SECOND INTERMEDIATE STAGE OF PRE-DOSING:
OUTWARD ENLARGEMENT OF HIGH-LUMINANCE PORTION IS FIXED, BUT LUMINANCE VALUE OF CENTRAL PORTION OF IMAGE DECREASES TO LET WHITE NOISE OR LIKE APPEAR AT CERTAIN PLACES.

(4) LATER STAGE OF PRE-DOSING:
NOISE VISIBLE AT CERTAIN PLACES OF SCREEN CENTER IN STAGE (3) ENLARGES AND INCREASES IN LUMINANCE. AS THIS BEHAVIOR IS EXHIBITED IMMEDIATELY BEFORE ELECTROSTATIC BREAKDOWN, PRE-DOSING SHOULD BE STOPPED AT THIS STAGE.

(5) OCCURRENCE OF ELECTROSTATIC BREAKDOWN:
ENTIRE SCREEN IS NOISY DUE TO OCCURRENCE OF ELECTROSTATIC BREAKDOWN. AT THIS STAGE, IT IS HIGHLY PROBABLE THAT PATTERN IS SERIOUSLY DAMAGED.

| CORRES-PONDENCE TO FIG. 2 | CORRES-PONDENCE TO FIG. 5 | OUTER CIRCLE | | INNER CIRCLE | |
|---|---|---|---|---|---|
| | | LUMINANCE CHANGE | AREA OR WIDTH ※ | LUMINANCE CHANGE | AREA OR WIDTH ※ |
| (1) | (1-1) | INCREASE | INCREASE | SAME AS OUTER CIRCLE | NONEXISTENT |
| (1) | (1-2) | STABLE | INCREASE | SAME AS OUTER CIRCLE | NONEXISTENT |
| (2) | (1-2) LATER STAGE | STABLE | STABLE | SAME AS OUTER CIRCLE | NONEXISTENT |
| (3) | (2-1) | STABLE | STABLE | DECREASE | INCREASE |
| (3) | (2-2) | STABLE | STABLE | STABLE ※ SIGNIFICANTLY AFFECTED BY NOISE | INCREASE |
| (4) | (2-2) LATER STAGE | NOISY | NONE | NOISY | NONE |
| (5) | | | | | |

CHARGED PARTICLE RADIATION APPARATUS

BACKGROUND OF THE INVENTION

1. Field of the Invention

The present invention relates to a charged particle radiation apparatus and, more specifically, to a charged particle radiation apparatus having a beam irradiation condition determination device that determines beam irradiation conditions for charging a sample.

2. Description of the Related Art

In recent years, a wide variety of patterns are used for semiconductor wafers and other samples as semiconductor elements are increasingly highly integrated and miniaturized. In addition, the importance of semiconductor element measurement and inspection is increasing as the semiconductor elements are increasingly highly integrated and miniaturized. Further, as the semiconductor elements are increasingly highly integrated and miniaturized, contact holes performing a function of establishing an electrical connection between multiple layers and grooves formed between line patterns are increasing in depth. The contact holes, in particular, are formed to a considerable depth with their diameter decreased. The aspect ratio (the ratio between the depth and diameter) of some contact holes is higher than 50.

A preliminary charging method (hereinafter may be referred to as the pre-dose method) is known as a method of measuring and inspecting the bottom of such deep holes and deep grooves. The pre-dose method, which is disclosed, for instance, in Japanese Patent No. 4093662 (U.S. Pat. No. 7,977,632), is a method of positively charging a beam irradiation region by irradiating a sample with a beam having a secondary electron emission efficiency (electrons emitted from a sample/electrons incident on the sample) of higher than 1 before beam irradiation for measurement or inspection. Electrons emitted from the bottom due to positive charging are directed toward the surface of the sample without colliding with the sidewall of a deep hole. Therefore, the electrons emitted from the bottom of the hole can be detected with high efficiency.

If the surface of the sample is excessively charged, the potential difference of one region from another region having a different potential may increase to cause electrostatic breakdown. Japanese Patent No. 5117080 (U.S. Pat. No. 8,384, 030) describes a preliminary charging condition determination method. This method performs pre-dosing and observation while changing the location of irradiation. When the luminance value of the bottom of a hole pattern increases above a setting, this method concludes that electrostatic breakdown may occur, and then decreases, for instance, a beam acceleration voltage for the purpose of reducing the effect of surface charging.

A method disclosed in Patent WO 2013/011792 A1 acquires images while changing beam conditions and analyzes the acquired images in order to determine pre-dose conditions under which the luminance value difference between an edge peak and a hole bottom is within a predetermined range.

SUMMARY OF THE INVENTION

As the aspect ratio, for instance, of a deep hole becomes high, it is demanded that the pre-dose method further enhance the effect of raising secondary electrons. Meanwhile, excessive charging causes electrostatic breakdown. It is therefore necessary to achieve charging in such a manner as to avoid electrostatic breakdown. Japanese Patent No. 4093662 (Corresponding to U.S. Pat. No. 7,977,632) does not describe a method of maintaining a high efficiency of secondary electron raising without causing electrostatic breakdown. A method described in Japanese Patent No. 5117080 (Corresponding to U.S. Pat. No. 8,384,030) makes it possible to determine pre-dose conditions that may suppress the possibility of electrostatic breakdown. However, this method scans an observation beam after pre-dosing to verify a pre-dosed state. Therefore, even if a pre-dose beam is irradiated after a desired pre-dosed state, the pre-dosed state cannot be verified until the observation beam is scanned. For example, the pre-dosed state prevailing immediately before electrostatic breakdown is a state where the sample is charged to the highest extent in a situation where electrostatic breakdown does not occur. Such a state is an optimal state from the viewpoint of the effect of raising secondary electrons. However, it is difficult to precisely verify such an optimal state until the observation beam is scanned to determine the charged state. Patent WO 2013/011792 A1 does not describe a method of determining the beam conditions for suppressing electrostatic breakdown. Further, Patent WO 2013/011792 A1 is similar to Japanese Patent No. 5117080 (U.S. Pat. No. 8,384,030) in that the pre-dosed state cannot be evaluated until the observation beam is scanned.

A charged particle radiation apparatus proposed below achieves proper charging while suppressing electrostatic breakdown.

In accomplishing the above object, according to one aspect of the present invention, there is provided a charged particle radiation apparatus for acquiring signal waveform data or image data of a pattern formed on a sample in accordance with charged particles, which are obtained by scanning a charged particle beam emitted from a charged particle source. The charged particle radiation apparatus includes a control device that switches between a first charged particle beam and a second charged particle beam. The first charged particle beam is scanned to acquire the image data. The second charged particle beam is scanned over the sample before the scan of the first charged particle beam and used to charge the sample more than the first charged particle beam. The control device acquires at least one of signal waveform data and image data about a pattern formed on the sample in accordance with a scan performed on the sample by the second charged particle beam. When the acquired data has proved to be indicative of a predetermined state, the control device stops the scanning of the second charged particle beam or registers on a predetermined storage medium the timing at which the acquired data has proved to be indicative of the predetermined state as a scan stop timing for the second charged particle beam.

The above-described configuration makes it possible to achieve proper charging while suppressing electrostatic breakdown.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

A charged particle radiation apparatus according to an embodiment of the present invention, which has a pre-dose function, will now be described in detail. A pre-dose method is a method of irradiating a sample with a beam in order to charge the sample before the beam is scanned to measure and inspect, for instance, a pattern formed on the sample. For example, a scanning electron microscope, which is one type of charged particle radiation apparatus, mainly detects secondary electrons that are excited when a sample, which is an observation target, is irradiated with a primary electron beam (hereinafter referred to as the "electron beam"). When the shape of a contact hole having a high aspect ratio is observed, the amount of electron beam incident on the bottom of the hole is smaller than the amount of electron beam incident on the surface layer of the sample due, for instance, to the inclination of the incident electron beam and the inclination of a formed hole pattern. Further, the secondary electrons excited from the bottom of the hole collide with the sidewall of the hole pattern and disappear before they reach a detector of the scanning electron microscope. As a result, a secondary electron signal indicative of the shape of the bottom of the hole may be insufficiently detected in some cases.

The pre-dose method is adopted in the above-described case. More specifically, an electron beam is preliminarily irradiated before the electron beam is irradiated for observation and measurement purposes, in order to bring the secondary electrons generated near the bottom of the hole up to the surface of the sample. An observation/measurement region (or a larger region including the observation/measurement region) is then positively charged. This makes it easy to bring up the secondary electrons from the bottom of the contact hole.

The pre-dose method positively charges the surface of the sample, for instance, by preliminarily irradiating a region larger than the observation region with an electron beam or by preliminarily irradiating the sample with an electron beam having a secondary electron emission efficiency of higher than 1.0. After the surface of the sample is charged by pre-dosing, measurement and inspection should be conducted while the sample surface is charged. Hence, measurement and inspection are conducted by scanning a beam having a secondary electron emission efficiency of close to 1.0 unlike a pre-dose beam.

Meanwhile, if a positive charge is excessively formed by pre-dosing, electrostatic breakdown may occur due to discharging. More specifically, if an excessive potential difference arises, for instance, between the positively charged sample surface and the bottom of the hole, a discharge occurs therebetween. It is preferred that a proper charge be formed without causing electrostatic breakdown. For example, a charge formed on the sample surface immediately before electrostatic breakdown is in an optimal state from the viewpoint of the effect of raising secondary electrons. If a proper charge is formed on the sample for the above-mentioned measurement and inspection, measurement and inspection can be conducted in a manner desired by an operator.

A scanning electron microscope capable of determining proper pre-dose conditions will now be described with reference to an accompanying drawing.

Figure 8:
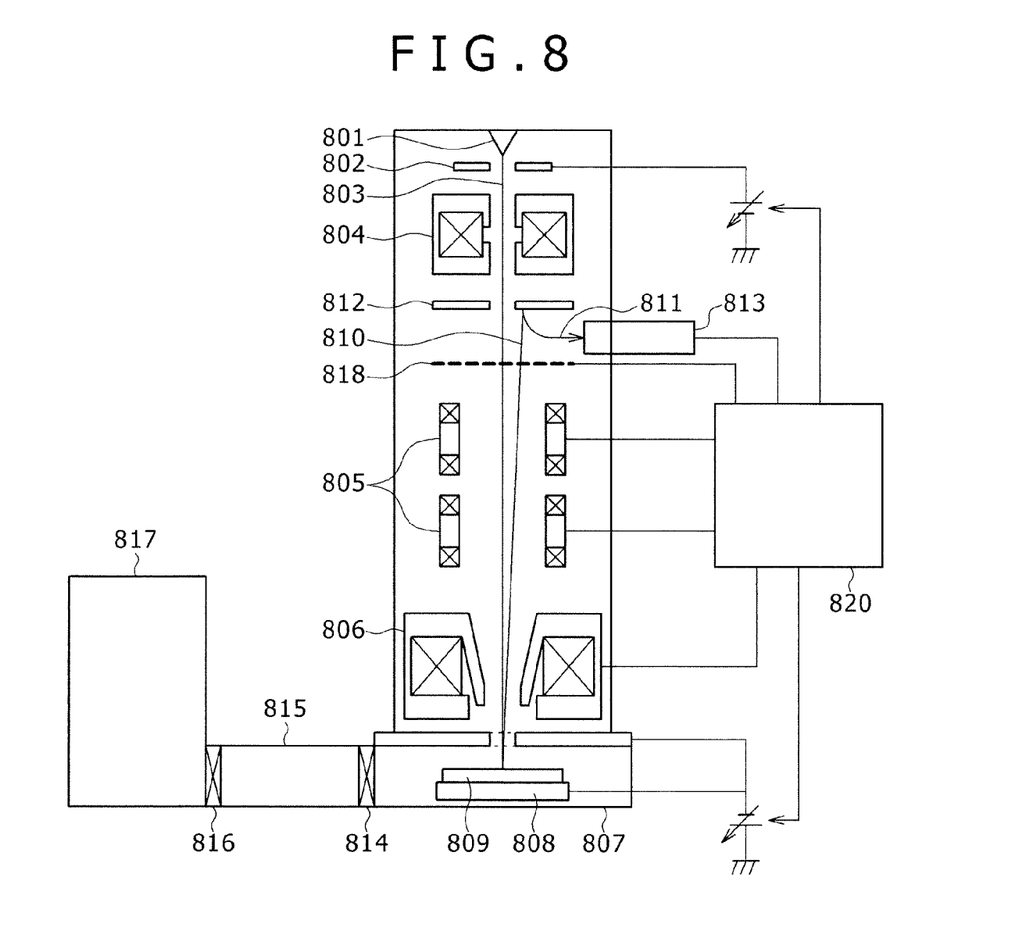
FIG. 8 is a diagram illustrating the outline of a scanning electron microscope (SEM)

FIG. 8 is a diagram illustrating the outline of a scanning electron microscope. An electron beam 803 is extracted from an electron source 801 by an extraction electrode 802, accelerated by an acceleration electrode (not shown), focused by a condenser lens 804, which is one type of focusing lens, and then scanned one-dimensionally or two-dimensionally over a sample 809 by a scanning deflector 805. The electron beam 803 is not only decelerated by a negative voltage applied to an electrode built in a sample stage 808, but also focused by the lens action of an objective lens 806 and irradiated onto the sample 809.

When the electron beam 803 is irradiated onto the sample 809, electrons 810, such as secondary electrons and backscattered electrons, are emitted from an irradiated spot. The emitted electrons 810 are accelerated in a direction toward the electron source by an acceleration action based on a negative voltage applied to the sample. The accelerated electrons 810 collide with a conversion electrode 812 to generate secondary electrons 811. The secondary electrons 811 emitted from the conversion electrode 812 are captured by a detector 813. The output of the detector 813 varies with the amount of captured secondary electrons. The luminance of a display device (not shown) varies with the output. When, for instance, a two-dimensional image is to be formed, the image of a scanning region is formed by synchronizing a deflection signal to the scanning deflector 805 with the output of the detector 813.

A deflection signal for moving a field of view may be superimposed on a deflection signal for performing a two-dimensional scan within the field of view and supplied to the scanning deflector 805. Deflection provided by this deflection signal is also referred to as "image shift deflection" and can be used to reposition the field of view of an electron microscope without operating, for instance, the sample stage to move the sample. In the present embodiment, it is assumed that image shift deflection and scanning deflection are provided by a single deflector. Alternatively, however, an image shift deflector and a scanning deflector may be separately provided.

An energy filter 818 for subjecting electrons emitted from the sample to energy discrimination is disposed between the sample 809 and the conversion electrode 812. The energy filter 818 includes, for example, three mesh electrodes and forms an electric field that reflects electrons moving toward the conversion electrode 812. The energy of passable electrons can be adjusted by adjusting the voltage to be applied to the mesh electrode.

In the example of FIG. 8, it is assumed that electrons emitted from the sample are converted by the conversion electrode before being detected. However, the present invention is not limited to such a configuration. For example, an alternative configuration may be employed so that the detection surface of an electron multiplier or other detector is placed in the orbit of accelerated electrons.

A control device 820 is capable of not only controlling the components of the scanning electron microscope, but also forming an image in accordance with detected electrons and measuring the pattern width of a pattern formed on the sample in accordance with a line profile, which is the intensity distribution of detected electrons. Further, the scanning electron microscope includes a preliminary evacuation chamber 815 and a mini-environment device 817. When the sample is to be introduced into a sample chamber 807, the preliminary evacuation chamber 815 pre-evacuates a sample atmosphere and the mini-environment chamber 817 forms a clean air space. In addition, vacuum valves 814, 816 are disposed between the two chambers for vacuum locking purposes.

Figure 9:
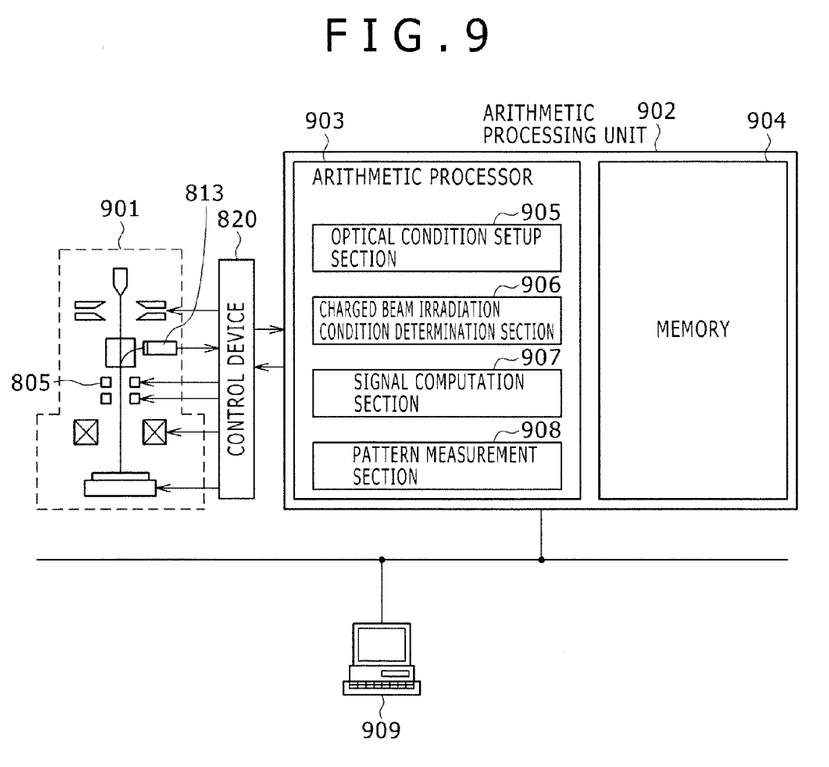
FIG. 9 is a diagram illustrating the outline of a pattern measurement system including an SEM.

FIG. 9 is a diagram illustrating in detail a measurement or inspection system including a scanning electron microscope (SEM). This system includes a scanning electron microscope system, which has an SEM main body 901, a control device 820 for the SEM main body, and an arithmetic processing unit 902. The arithmetic processing unit 902 includes an arithmetic processor 903 and a memory 904. The arithmetic processor 903 supplies a predetermined control signal to the control device 820 and processes a signal derived from the SEM main body 901. The memory 904 stores image information acquired and recipe information. In the present embodiment, it is assumed that the arithmetic processing unit 902 is separate from the control device 820. However, an alternative is to use a one-piece control device, which incorporates the functionality of the arithmetic processing unit 902.

Electrons emitted from the sample or electrons generated by the conversion electrode are captured by the detector 813 and converted to a digital signal by an analog-to-digital converter built in the control device 820. Image processing hardware built in the arithmetic processing unit 902, such as a CPU, ASIC, or FPGA, performs image processing depending on the intended purpose.

The arithmetic processor 903 includes an optical condition setup section 905 and a charged beam irradiation condition determination section 906. The optical condition setup section 905 sets optical conditions for the SEM in accordance, for instance, with measurement conditions input from an input device 909. The charged beam irradiation condition determination section 906 determines later-described charged beam irradiation conditions.

Further, the arithmetic processor 903 includes a signal computation section 907 that evaluates dynamic image changes in accordance with image data and signal waveform data. The signal computation section 907 compares, for example, image data (first image) acquired at a first timing and image data (second image) acquired at a second timing, which is different from the first timing, and evaluates the amount of change in the image data. More specifically, the signal computation section 907 evaluates the image data acquired at different timings, and then measures beam irradiation time and the number of frames when no more change is found in the images acquired at the different timings or the amount of change is not greater than a predetermined value. The measured beam irradiation time and the measured number of frames are registered in the memory 904.

Furthermore, the arithmetic processor 903 includes a pattern measurement section 908 that measures the dimensions of a pattern in accordance with an acquired signal waveform. The pattern measurement section 908 forms a line profile in accordance, for instance, with a detected signal and measures the dimension between peaks in the line profile.

A display device provided for the input device 909, which is connected to the arithmetic processing unit 902 through a network, displays a GUI that presents, for instance, images and inspection results to the operator.

Some or all of control and processing functions of the arithmetic processing unit 902 may be allocated to a computer having a CPU and a memory capable of storing images for the purpose of letting the computer exercise such functions. Another alternative is to use one computation device that exercises the functions of both the control device 820 and the arithmetic processing unit 902. The input device 909 also functions as an imaging recipe creation device that defines an imaging recipe indicative of measurement conditions, including the coordinates of an electronic device required, for instance, for inspection, the type of pattern, and imaging conditions (optical conditions and state movement conditions).

The signal computation section 907 digitizes an image derived from pre-dosing, defines determination conditions for optimal image acquisition (and for the prevention of electrostatic breakdown) in accordance with the behavior of the obtained numerical value, determines an optimal pre-dose time in accordance with an image derived from an ongoing pre-dose process for actual pre-dosing, generates a control signal for bringing the pre-dose process to an automatic stop when the conditions are met, and transmits the control signal to the control device 820.

Figure 2:
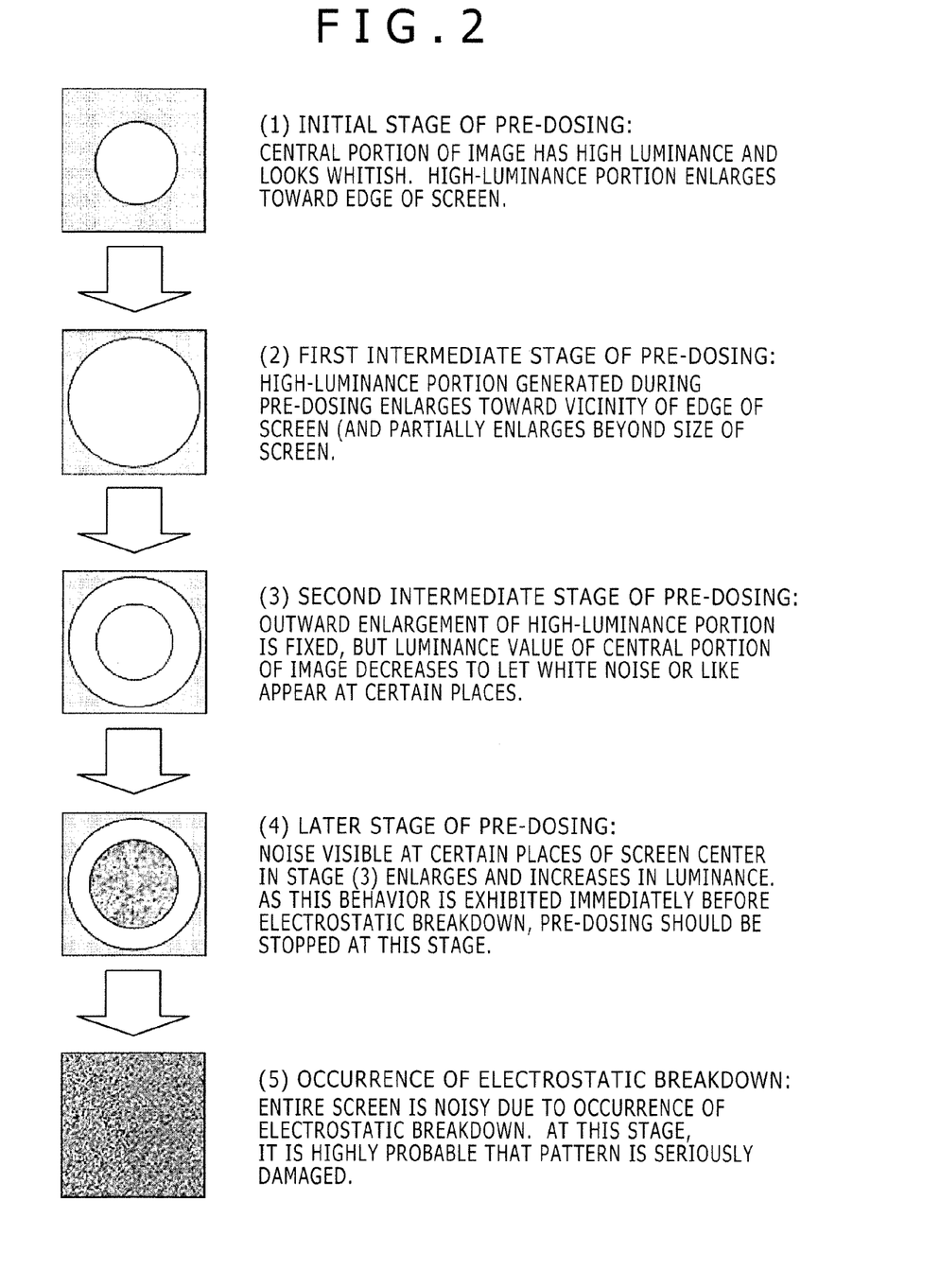
FIG. 2 is a set of diagrams illustrating image changes that occur when a pre-dose beam is scanned over a sample.

FIG. 2 is a set of diagrams illustrating image changes that occur when pre-dosing is performed. Images exemplified in FIG. 2 are formed in accordance with a detection signal derived from pre-dose beam scanning. In general, a pre-dose beam scan and a measurement/inspection beam scan are performed at different timings and under different beam conditions. In the present embodiment, however, the pre-dose beam scan is performed to achieve pre-dosing and image formation (signal waveform generation) for the purpose of determining proper pre-dose conditions. When the image features exemplified in FIG. 2 are encountered or when a predetermined period of time elapses after the extraction of the image features, the optical condition setup section 905 transmits a control signal to the control device 820 in order to stop the irradiation of a pre-dose beam (a second charged particle beam) and start the scan of a pattern measurement/inspection beam (a first charged particle beam). FIG. 2 shows examples of an image obtained when the pre-dose beam is scanned over a circular hole pattern.

(1) Initial Stage of Pre-Dosing

The effect of pre-dosing increases with an increase in the area for preliminary irradiation (with a decrease in the magnification). It is therefore presumed that pre-dosing is performed at a low magnification. When pre-dosing starts, the luminance circularly increases beginning with the center of a screen and becomes white (black, white, and other expressions of the screen are defined on the basis of a 256-step grayscale). The area of the resulting circular shape depends on the magnification and imaging conditions.

(2) First Intermediate Stage of Pre-Dosing

The dynamic enlargement of a high-luminance portion, which starts at the beginning of pre-dosing, comes to a stop when it progresses to a certain extent. Depending on the imaging conditions, the high-luminance portion may not remain within the screen and partially enlarge beyond the size of the screen.

(3) Second Intermediate Stage of Pre-Dosing

The above-mentioned enlargement of the high-luminance portion comes to a stop, and then the luminance value of a hole pattern center decreases so that the generation of a noise component starts.

(4) Later Stage of Pre-Dosing

The noise component generated near the center of the screen, which is confirmed in stage (3), enlarges outward from the center of the screen. At the same time, the luminance of the noise component greatly changes. This phenomenon is a behavior that occurs immediately before electrostatic breakdown. At this stage, the effect of pre-dosing is maximized. It is preferred that the pre-dosing be stopped at this stage to perform an imaging process under observation/measurement conditions.

(5) Occurrence of Electrostatic Breakdown

Electrostatic breakdown has occurred in an electron beam irradiation region because of excessive pre-dosing. It means that the pattern to be measured is broken. It is essential that the pre-dosing be stopped before the occurrence of this phenomenon.

Figure 3:
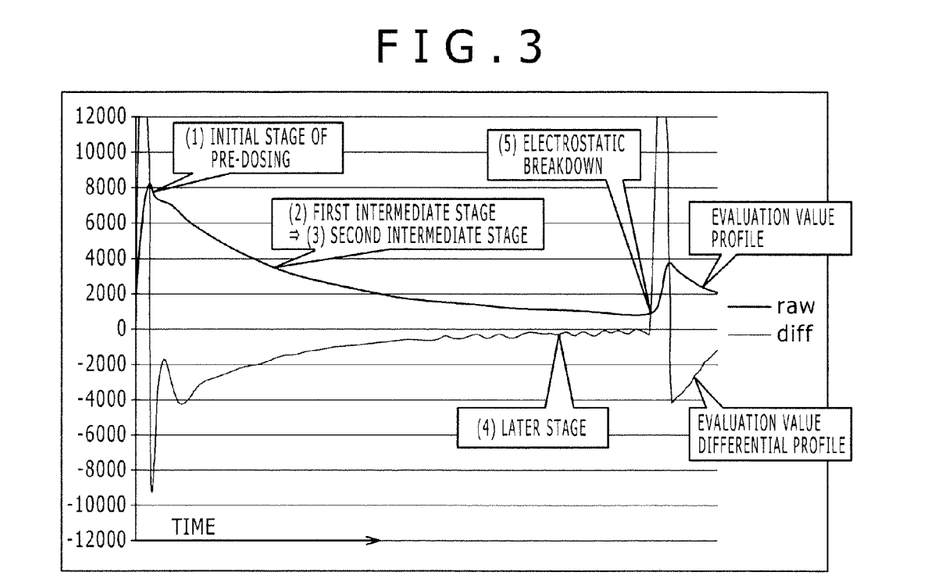
FIG. 3 is a graph illustrating temporal changes in an image evaluation value of an image obtained when a pre-dose beam is scanned over a sample.

FIG. 3 is a graph that quantifies the image changes shown in FIG. 2. A heavy solid line named "EVALUATION VALUE PROFILE" is obtained when the variance of the whole image is plotted in the graph. A line named "EVALUATION VALUE DIFFERENTIAL PROFILE" is obtained when the amount of change in the variance is plotted in the graph. The vertical axis represents an evaluation value (dimensionless), and the horizontal axis represents pre-dose time.

Attention should be focused on the (4) later stage of pre-dosing. Observing the "EVALUATION VALUE DIFFERENTIAL PROFILE" reveals that numerical values are unstable due to the influence of noise. The values of both the "EVALUATION VALUE PROFILE" and the "EVALUATION VALUE DIFFERENTIAL PROFILE" are suddenly increased after an unstable behavior of the differential profile. It indicates that electrostatic breakdown has occurred.

Dynamic image changes exemplified in FIGS. 2 and 3 are substantially the same irrespective of the employed sample (for example, wafer), the measurement position, the order of measurement, or the like although they differ in the evaluation value and time. Therefore, when, based on the information described above, pre-dosing comes to an automatic stop while the optimal state prevails, stable pre-dosing can be achieved.

Optimal conditions may be set, for example, by lucidly calculating the maximum and minimum evaluation values prevailing after pre-dosing, defining a threshold value on a percentage basis relative to the results of calculation, and defining the conditions prevailing when the evaluation value crosses the threshold value as the optimal conditions (the optimal pre-dose time).

Figure 4:
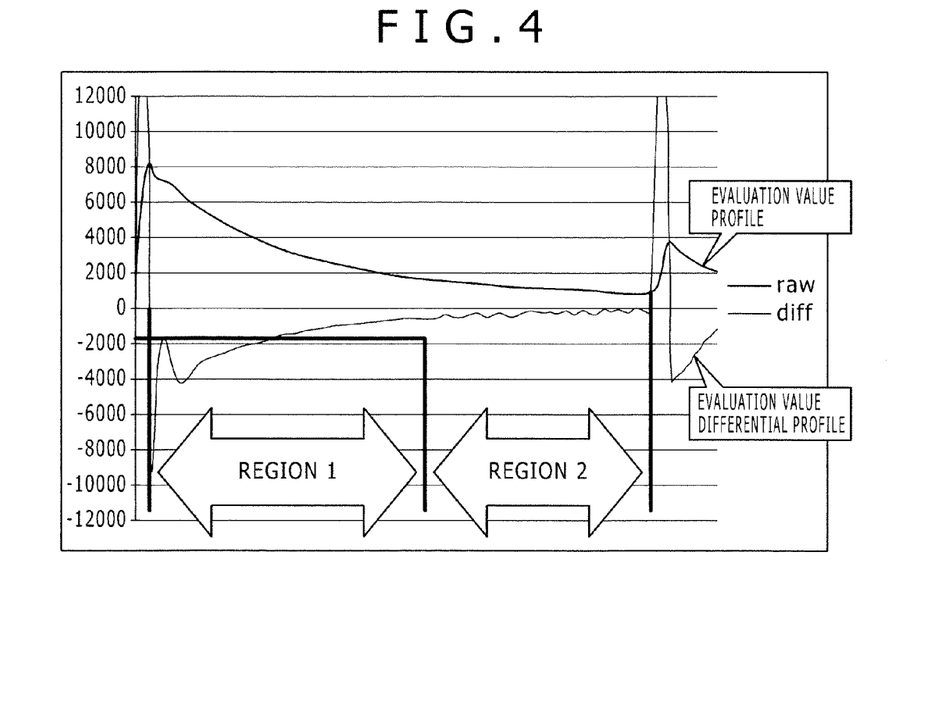
FIG. 4 is a graph illustrating temporal changes in the image evaluation value of an image obtained when a pre-dose beam is scanned over a sample.

Further, at the aforementioned (4) later stage of pre-dosing, the evaluation value graph is unstable as the value significantly moves the graph up and down (see region 2 in FIG. 4). When a determination process based on the aforementioned threshold value is applied to this region, the determination conditions are often met earlier or later than the actual optimal conditions due to the influence of noise. Thus, inspection images cannot be steadily obtained. Hence, different evaluation calculation processes are performed on region 1 where the graph shown in FIG. 4 is stable and region 2 where the graph shown in FIG. 4 is unstable as the value significantly moves the graph up and down. For example, the aforementioned threshold value determination method may be applied to region 1 while a method of simply stopping the pre-dosing after the lapse of a predetermined period of time is applied to region 2.

An alternative is to stabilize the evaluation value profile by smoothing the last several results of evaluation value calculations and apply the determination process based on the aforementioned threshold value.

When, as described above, temporal changes in the amount of image features are determined in accordance with images derived from pre-dose beam scanning to make the pre-dose conditions definable on the basis of the resulting data, proper pre-dosing stop time can be set. If an attempt is made to evaluate a charged state with an observation beam after pre-dosing, it is conceivable that the charged state may change during observation as well. Therefore, when this method of performing both a preliminary charging process and a charge evaluation process with a pre-dosing beam is employed, it is possible to derive a pre-dose stop timing based on a proper charge evaluation.

Figure 5:
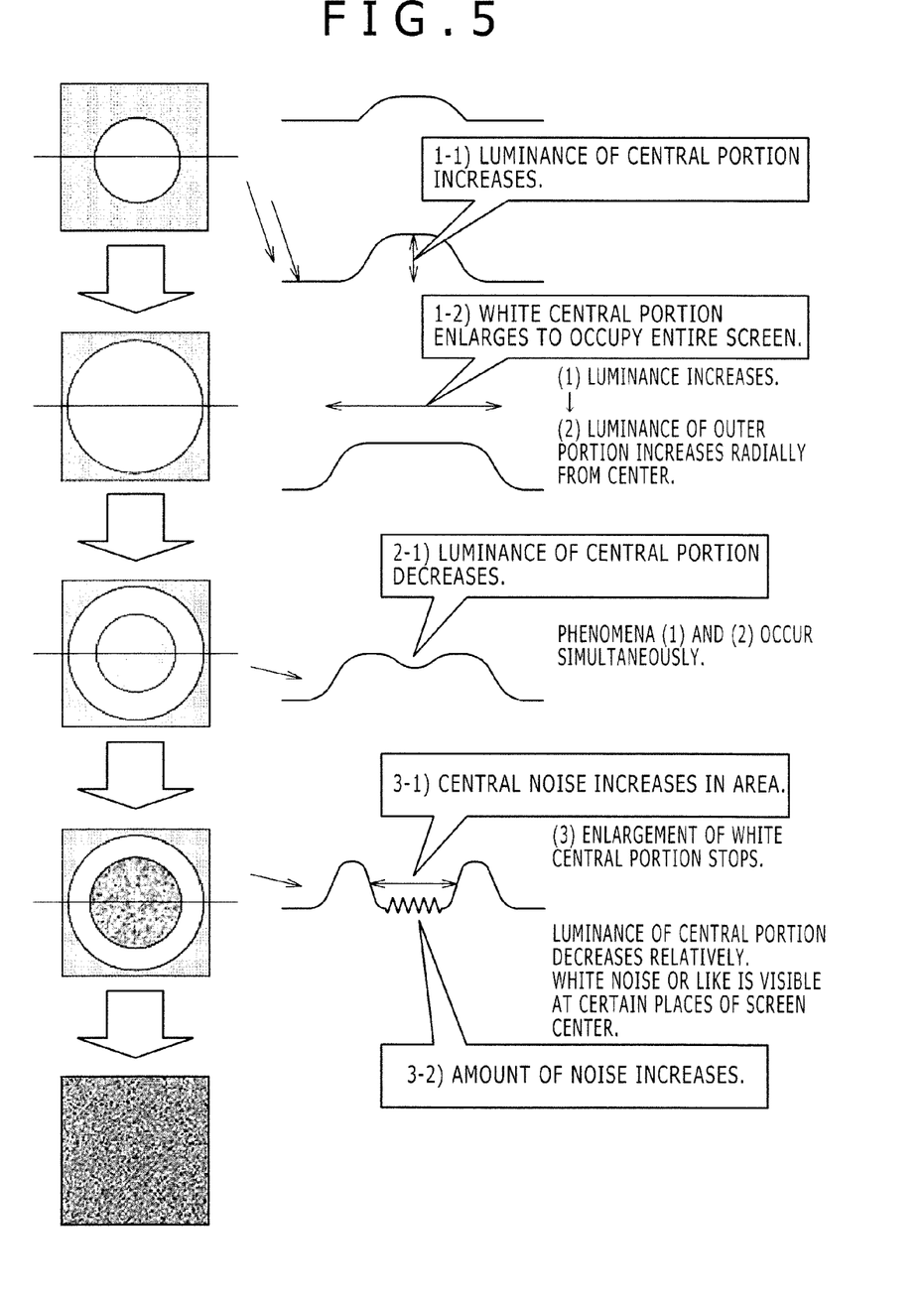
FIG. 5 is a set of diagrams illustrating changes in a signal waveform obtained when a pre-dose beam is scanned over a sample.

FIG. 5 is a set of diagrams illustrating changes in a waveform signal that occur in a different pre-dosed state. After the start of pre-dosing, the luminance of an image center increases (1-1), and then the area of a white circular portion radially enlarges from the image center (1-2).

The size of the above-mentioned white circular portion depends on the pre-dose conditions (the magnification and the degree of defocusing). The reason is that surface charging has progressed because of pre-dosing in the field of view. When pre-dosing is insufficient, the area and luminance of the white circular portion changes. Therefore, it is possible to measure the amount of change in the area and luminance (or the enlargement of a high-luminance portion in a luminance profile near the center of the screen) and use a differential value or the like to conclude that pre-dosing is insufficient until the amount of change decreases below a certain level. This degree of pre-dosing may be sufficient depending on the purpose of measurement and the type of sample. Therefore, the time at which the amount of change in the enlargement of the high-luminance portion is zero or not larger than a predetermined value may be defined as the pre-dose time for measuring the sample. In the present embodiment, the amount of change (differential value) caused a change in the evaluation value is adopted as an evaluation criterion. Consequently, the present embodiment makes it possible to derive proper pre-dose time without regard to the performance of the pattern.

Next, at an intermediate stage of pre-dosing, the luminance of a central portion of a hole decreases (2-1). In this instance, the amount of change in the luminance of the boundary of a white circular portion is small; however, the luminance of a central portion of the screen decreases. It means that a surface charge provided by pre-dosing is gradually approaching an optimal state. Next, noise is generated near the center of the hole (2-2). In this instance, a noise-like phenomenon occurs near the center of the screen. This phenomenon not only represents a state where the effect of pre-dosing is evident, but also indicates that the pre-dosing is close to its limit and about to cause electrostatic breakdown. The phenomenon described under (2-1) continues so that the luminance of the outer circumference of the center of the screen is still high. However, a low-luminance portion (a region where a noise-like phenomenon is visible) at the center of the screen radially enlarges.

When the enlargement stabilizes and the noise at the center of the screen increases, electrostatic breakdown occurs. The resulting state is as shown at (5) in FIG. 2.

As such being the case, when items indicated in later-described table are managed with respect to an image (or a luminance profile) that is currently subjected to pre-dosing, it is possible to steadily determine optimal pre-dose conditions.

A desired image may be obtained from some samples even if pre-dosing is not performed to incur a state where electrostatic breakdown is about to occur as indicated at (4) in FIG. 2. Hence, it is possible to perform pre-dosing under conditions that incur, for example, stage (2) or (4) in FIG. 2, and set pre-dose time accordingly.

Figure 6:
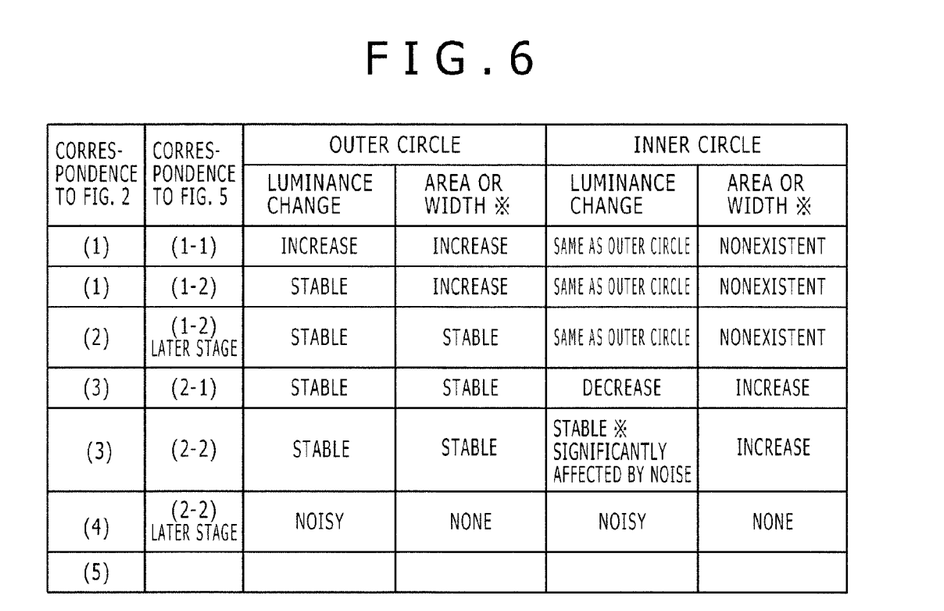
FIG. 6 is a table illustrating image feature changes caused during the progress of pre-dosing.

FIG. 6 is a table illustrating changes in image evaluation items that occur during pre-dosing. When the pre-dose conditions are determined in accordance with image evaluation values derived from various stages of pre-dosing, as indicated in the table, it is expected that the effect of pre-dosing will be steadily produced without significantly depending on sample changes.

If, for instance, stage (2) in FIG. 2 can be determined to be a proper pre-dosed state, stages up to stage (1-2) in FIG. 5 should be monitored while focusing attention only on changes in an outer circle. Similarly, if the pre-dose conditions indicated in stage (1-2) in FIG. 5 are sufficient, a sufficiently stable effect of pre-dosing can be obtained by managing an index value indicated at (2-2) in FIG. 6.

In the present embodiment, when the amount of change in the index value and the noise evident immediately before electrostatic breakdown are targeted for evaluation, stable pre-dose conditions can be derived irrespective of pattern shape changes due, for instance, to process variation. The width of "AREA OR WIDTH" can be determined by regarding a certain percentage of the maximum and minimum values (for example, (maximum value−minimum value)×50%) of cross-sectional luminance as a threshold value, searching outward from a central portion to check whether the threshold value is exceeded, and determining the interval between positions at which the threshold value is initially exceeded.

Figure 1:
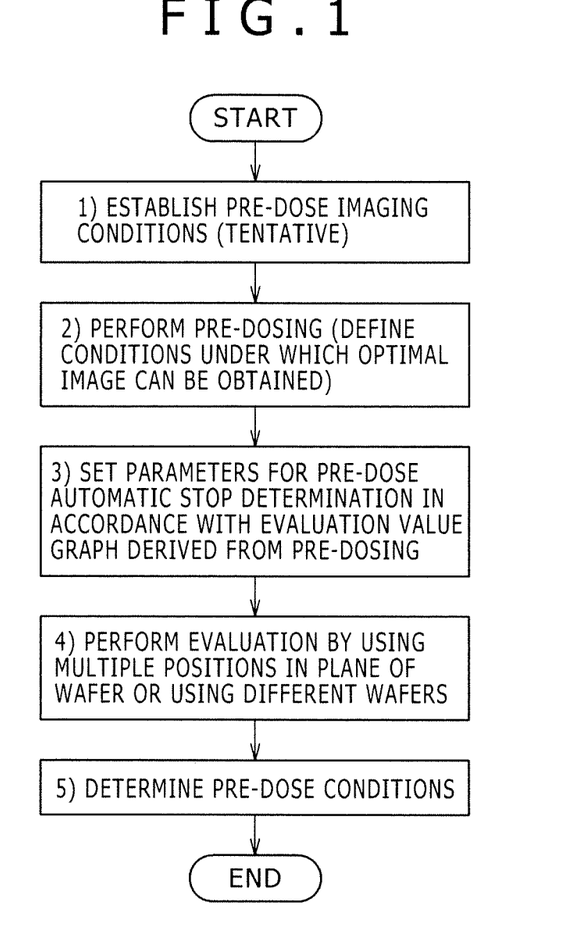
FIG. 1 is a flowchart illustrating a process in which a charged particle beam is scanned to derive proper irradiation conditions for the charged particle beam while a sample is preliminarily charged.

A procedure for setting the pre-dose conditions in accordance with the evaluation of an image currently subjected to pre-dosing will now be described. FIG. 1 is a flowchart illustrating the procedure. In the present embodiment, it is assumed that five different spots in the plane of a semiconductor wafer are measured under the same conditions. It is also assumed in the present embodiment that all measurement spots have the same shape and are observed and measured under the same conditions.

For example, seven different timings may be defined as the pre-dose stop timing. The first timing is a timing at which the change in luminance is smaller than a predetermined change. The second timing is a timing at which a predetermined period of time has elapsed after the first timing. The third timing is a timing at which the change in the size of a high-luminance portion within the scan range of the charged particle beam is smaller than a predetermined size. The fourth timing is a timing at which a predetermined period of time has elapsed after the second timing. The fifth timing is a timing at which the luminance of the high-luminance portion is not higher than a predetermined value, the luminance of a central portion of the high-luminance portion is lower than the luminance of an outer region of the high-luminance portion, or the luminance ratio between the outer region of the high-luminance portion and the central portion of the high-luminance portion agrees with a predetermined ratio. The sixth timing is a timing at which a predetermined period of time has elapsed after the fifth timing. The seventh timing is a timing at which the noise of the high-luminance portion is in a predetermined state.

(Procedure 1) Establishing Pre-Dose Imaging Conditions (Tentative)

Set final observation/measurement imaging conditions in advance, and then determine the pre-dose conditions (acceleration voltage, current value, magnification, pre-dose time, etc.). First of all, determine conditions under which an optimal image can be obtained at a specific position of the sample to be observed and measured.

(Procedure 2) Performing Pre-Dosing (Defining Conditions Under which an Optimal Image can be Obtained)

Perform pre-dosing with respect to the sample. If pre-dosing is performed a number of times at the same spot or in a region including the same spot, electrostatic breakdown or the like may occur to seriously damage the pattern. Therefore, change the pre-dosing spot each time or exercise similar care to avoid damage to the pattern.

(Procedure 3) Acquiring Parameters for Pre-Dose Automatic Stop Determination

Perform pre-dosing to acquire an evaluation graph that looks like FIG. 3. For evaluation value calculation purposes, calculate the variance of one or more images currently subjected to pre-dosing. The evaluation value may be calculated from the average of a plurality of images in consideration of noise generated during SEM image acquisition. However, the use of the average causes noise components to be averaged. Therefore, it is preferred that the evaluation value be calculated from one or two images. Output an evaluation value graph (see FIG. 3) that indicates (1) the time elapsed after the start of pre-dosing, (2) evaluation value 1 (the variances of images), and (3) evaluation value 2 (the difference between the variances of the images) of currently performed pre-dosing. When a test sample or other sample whose breakdown is tolerable, it is preferred that the evaluation value graph be obtained after actually allowing electrostatic breakdown to occur. The noise of an image extracted through variance evaluation is generated immediately before electrostatic breakdown. Therefore, the pre-dose stop timing can be determined at a timing at which the noise component meets predetermined conditions so that the greatest charge is formed on the sample without causing electrostatic breakdown. Further, the amount of change in the noise area may be monitored so as to generate a signal that stops the pre-dosing when an increase in the noise area exceeds a predetermined value.

(Procedure 4) Performing Proper Evaluation of Parameters, for Instance, in the Plane of a Wafer Determine the optimal pre-dose conditions by using the evaluation value graph that is acquired by performing procedure 3. An example of a procedure for determining the optimal conditions will be described later.

(Procedure 5) Determining the Pre-Dose Conditions

In conclusion, set the optimal conditions that are acquired by performing procedures 1 to 4. A simple procedure for setting the optimal conditions would be to calculate the maximum and minimum values from the evaluation value graph acquired by performing procedure 3, determine the intersection between the evaluation value graph and a certain percentage (%) of the maximum and minimum values, and define the determined intersection as a threshold value. When the maximum and minimum values are grasped to determine the threshold value as described in conjunction with the present embodiment, desired pre-dose conditions can be determined within such a range as to avoid the occurrence of electrostatic breakdown no matter what type of sample is used. Further, the evaluation graph exemplified in FIG. 3 shows the status of a sample that prevails before the occurrence of electrostatic breakdown. Therefore, as far as the input device 909 can be used to perform threshold value setup while viewing the evaluation graph displayed on the display device of the input device 909, proper pre-dose conditions can be set in accordance with the operator's intention.

It should be noted that an image currently subjected to pre-dosing changes as shown in FIG. 2. Such changes are quantified in the form of an evaluation graph and exemplified in FIG. 3. The evaluation graph obtained in the event of electrostatic breakdown, which is shown at (5) in FIG. 3, indicates that the image is entirely noisy with its numerical value significantly changed.

Under normal conditions, it is preferred that a point immediately before the occurrence of electrostatic breakdown be steadily measured. However, as indicated by the evaluation value graph of FIG. 3, the profile may become corrugated at the later stage of pre-dosing (4), which is immediately before the occurrence of electrostatic breakdown. Therefore, it may be difficult in a certain case to determine a threshold value that steadily detects a point immediately before stage (5).

In the above case, the evaluation value graph depicting the situation between the start of pre-dosing and the occurrence of electrostatic breakdown is divided into two regions as indicated in FIG. 4. Region 1 corresponds to the first intermediate stage of pre-dosing (2) and the second intermediate stage of pre-dosing (3), which are shown in FIG. 2 and subsequent to the start of pre-dosing. Region 2 corresponds to the later stage of pre-dosing (4) shown in FIG. 2.

As mentioned earlier, the evaluation value graph gradually rises or falls in region 1. In region 2, however, the evaluation value graph resembles a zigzag due to a noise-like signal resulting from surface charging based on pre-dosing.

Hence, the threshold value at the contact point between regions 1 and 2 is used as one parameter to determine the period of time required for region 2 to end. For region 1, for example, a certain percentage of the maximum and minimum values of the evaluation value graph is calculated as the threshold value. For region 2, the optimal pre-dose conditions are determined by setting a predetermined period of time after the end of region 1 (optimal pre-dose time). The above-described pre-dose automatic stop determination conditions are added to the pre-dose conditions defined by performing procedure 1, and the resulting conditions are applied as the pre-dose conditions.

An alternative is to perform this process at multiple points of a wafer, measure the threshold value of region 1 and the optimal stop time of region 2, and use the resulting average, maximum, or minimum value to define the pre-dose conditions. Another alternative is to divide the region shown in FIG. 3 into three or more regions in accordance with the amount of change in the graph and, for example, determine each region by using the threshold value or set a predetermined period of time for each region (a percentage of 50% or the like may be applied to the execution time for region 1).

Figure 7:
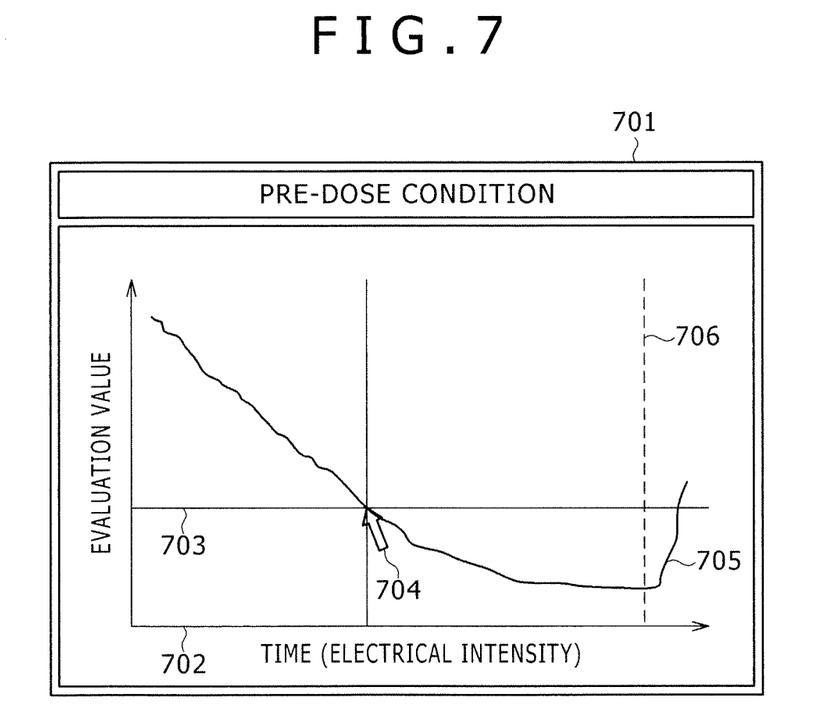
FIG. 7 is a diagram illustrating an example of a GUI (Graphical User Interface) screen for setting pre-dose conditions.

In addition, an example in which temporal changes in an image feature amount are made visible to set proper pre-dose conditions will now be described. FIG. 7 is a diagram illustrating an example of a GUI screen for setting pre-dose conditions. The GUI screen 701 exemplified in FIG. 7 appears, for example, on the display device of the input device 909. Image conditions for the signal computation section 907 to generate a pre-dose stop signal are set in accordance with the pre-dose conditions defined from the GUI screen. A graph 702 is displayed on the GUI screen 701. The vertical axis of the graph 702 represents an image evaluation value (luminance value, variance, or the like) and the horizontal axis represents pre-dose irradiation time. The graph 702 is prepared in accordance with data obtained when procedures 1 to 3 are performed. Information about the image feature amount and information about settings entered from the GUI screen are stored in the memory 904. A cross-hair cursor 703 can be moved along a graph indicative of the relationship between the image evaluation value and time of the graph 702. A pointer 704 is used to move the cross-hair cursor 703. Further, a borderline 706 is displayed on the shorter-time side of the point of electrostatic breakdown 705. The borderline 706 can be used to either prohibit a setting that is on the longer-time side of the borderline 706 or issue an alarm when a setting beyond the borderline 706 is selected. In this manner, the borderline 706 prevents the selection of a setting at which electrostatic breakdown may occur.

As described above, when setup is performed in accordance with actually acquired chronological image information, it is possible to set desired pre-dose conditions while reducing the possibility of electrostatic breakdown. For example, if predetermined conditions are not met within a predetermined period of time (if, for example, the amount of change in the size of the high-luminance region does not decrease to a predetermined value or smaller) in a situation where the pre-dose stop timing is set from the GUI screen exemplified in FIG. 7, it is preferred that a process be performed to stop the pre-dosing. For example, when the maximum pre-dose time set from a GUI screen (not shown) is reached, the pre-dosing should be stopped no matter whether predetermined image features are obtained. When this configuration is employed, a beam scan that causes a sample to electrostatically break down can be prohibited even if, for some reason, a phenomenon indicative of impending electrostatic breakdown cannot be recognized from an image.

In the present embodiment, optimal pre-dose irradiation conditions are determined by using the variance of the whole image and its difference. However, the optimal conditions may alternatively be determined by using parameters such as a different region and an evaluation function. For example, the optimal conditions may be determined by using the area of the whole high-luminance region indicated in FIG. 2, the amount of change in a noisy region (area), luminance changes in the noisy region, the variance of only the noisy region and luminance value changes, or the combination of these. The determined pre-dose irradiation conditions are stored, for instance, in the memory 904 and then read to perform pre-dosing.

Further, the above-described present embodiment has been described on the assumption that pre-dosing is performed with a critical dimension scanning electron microscope (CD-SEM) to observe and measure the diameter and shape of a contact hole in a semiconductor wafer and to determine whether or not the contact hole is open. However, the present embodiment is also applicable, for instance, to a general-purpose SEM, an FIB-SEM, a mask inspection device, and a review device.

The above-described present embodiment is not limited to the observation and measurement of contact holes, but is also applicable to the observation and measurement of the shape of a line and complicated shapes derived, for instance, from the combination of a line and a hole.

The pre-dose method can also increase the efficiency of secondary electron signal collection in the vicinity of the bottom of a contact hole having a high aspect ratio. However, even if pre-dosing is performed at a plurality of different locations within a wafer under the same imaging conditions, the effect of pre-dosing is not always constant for images obtained after the pre-dosing. For example, if the bottom of a hole at the center of a wafer can be adequately observed and the same conditions are applied to an edge of the wafer, the bottom of the hole at the edge of the wafer may not always be observed in the same manner as for the center of the wafer.

First of all, the above situation is attributable to a factor related to a sample, such as the variation in the shape of a pattern, the difference in the result of pattern formation, and subtle changes in the film pressure for pattern formation. However, if the position of a semiconductor wafer or other sample to be measured varies, the quality of images obtained under the same imaging conditions may vary.

Further, the electron dose irradiated by the same apparatus does not always remain constant. Even if the same apparatus is used, its condition changes with time. Therefore, even if image observation is conducted under the same conditions, acquired images are not always in the same expected condition. This also holds true when different apparatuses are used. When an electron beam scanning apparatus is used, electron beam irradiation conditions for image observation vary from one apparatus to another. In addition, the apparatus condition and observation conditions change with time. It is therefore necessary to make periodic adjustments to maintain optimal conditions.

Furthermore, when pre-dosing is performed, the sample is irradiated with a large amount of electron beam. Therefore, when a plurality of spots of the same wafer are continuously irradiated, it is conceivable that the condition of the wafer may change.

Moreover, if pre-dosing is excessively performed, electrostatic breakdown may occur, thereby causing serious damage to the sample. The phenomenon of electrostatic breakdown must be particularly avoided because it causes irreversible damage to the wafer.

When, in particular, automatic measurements are to be made, for instance, in a mass production process, it is preferred that the above-described problems be fixed to always perform pre-dosing under optimal conditions and acquire optimal images.

Figure 10:
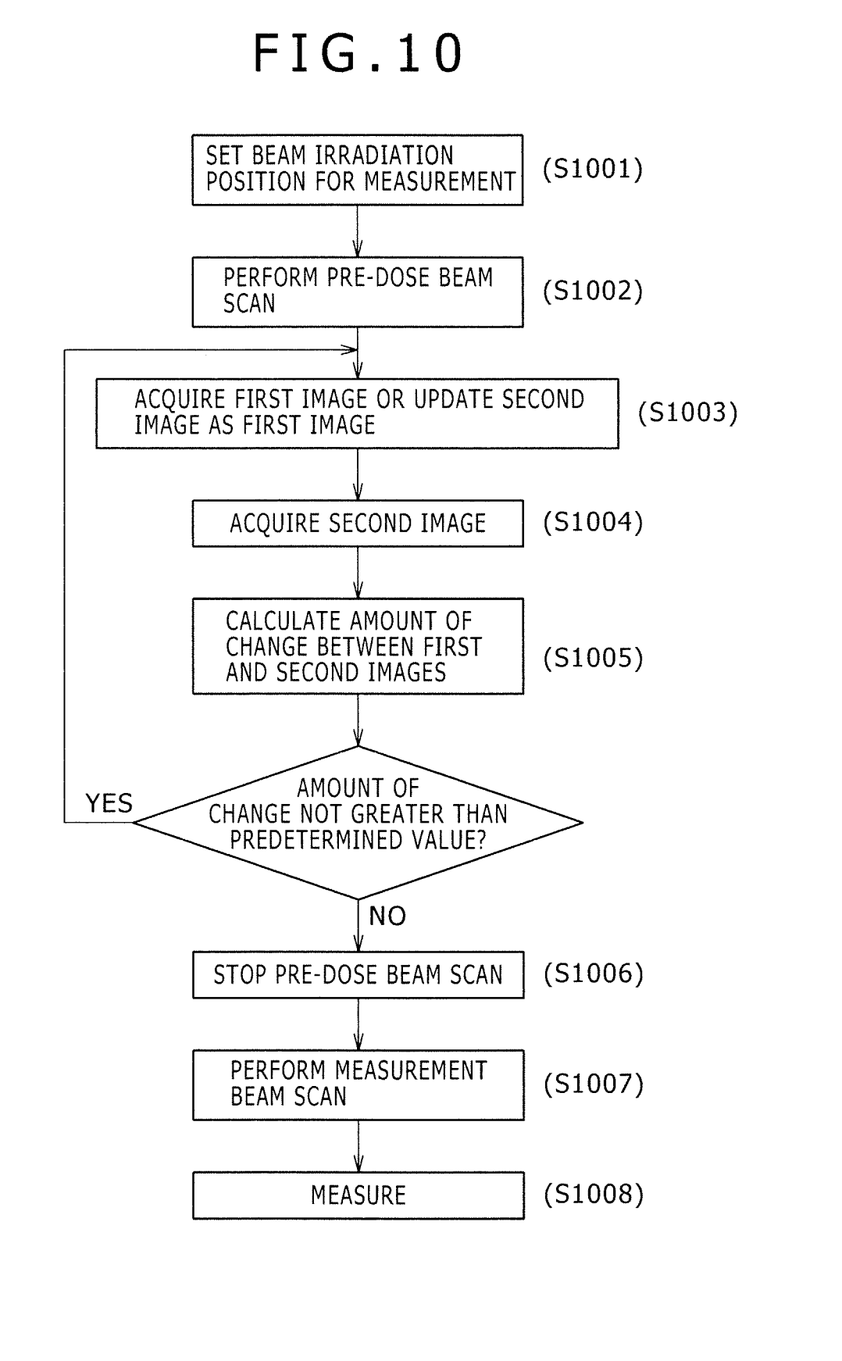
FIG. 10 is a flowchart illustrating a process in which pre-dose conditions are determined in real time during pre-dosing.

The present embodiment will now be described with reference to an example in which the pre-dose conditions are derived when pre-dosing is performed for actual measurement. FIG. 10 is a flowchart illustrating a process in which pre-dose beam stop timing is determined in a pre-dose process for pattern measurement. First of all, the sample stage and deflector are controlled so that a beam irradiation position is adjusted for a pattern on a semiconductor wafer that is to be measured (step 1001). Next, the pre-dose beam is scanned over the pattern to be measured to acquire a first image (steps 1002 and 1003). After the first image is acquired, a second image prevailing when pre-dosing progresses to a certain extent is acquired (step 1004). Next, for example, the size and luminance of a high-luminance portion at the center of a hole within the first and second images are calculated to determine the difference (the amount of change) between the first and second images (step 1005). If the difference per unit time is greater than a predetermined value, it means that charge formation by pre-dosing is in progress. Therefore, the second image is updated as the first image (step 1004), and then a new second image is acquired (step 1005).

As described earlier, when pre-dosing is performed, the high-luminance portion of an image enlarges over time after the start of the pre-dosing. When the pre-dosing progresses to a certain extent, the enlargement of the high-luminance portion comes to a stop. Therefore, the progress of pre-dosing can be grasped by evaluating the degree of enlargement. As the progress of pre-dosing before the occurrence of electrostatic breakdown can be grasped, the sample can be significantly charged to detect the secondary electrons with high efficiency while reducing the possibility of electrostatic breakdown.

Further, when changes in the luminance prevailing during a pre-dose process and in the area of the high-luminance portion are evaluated instead of merely determining the absolute value of luminance by using a threshold value, proper pre-dose stop conditions can be derived irrespective, for instance, of the performance of a hole. In other words, the progress of charging is evaluated in accordance with relative values obtained over time and not in accordance with a simple absolute value of luminance or the like. Hence, a stop process can be determined with a minimum of error irrespective of the performance of a pattern.

Figure 11:
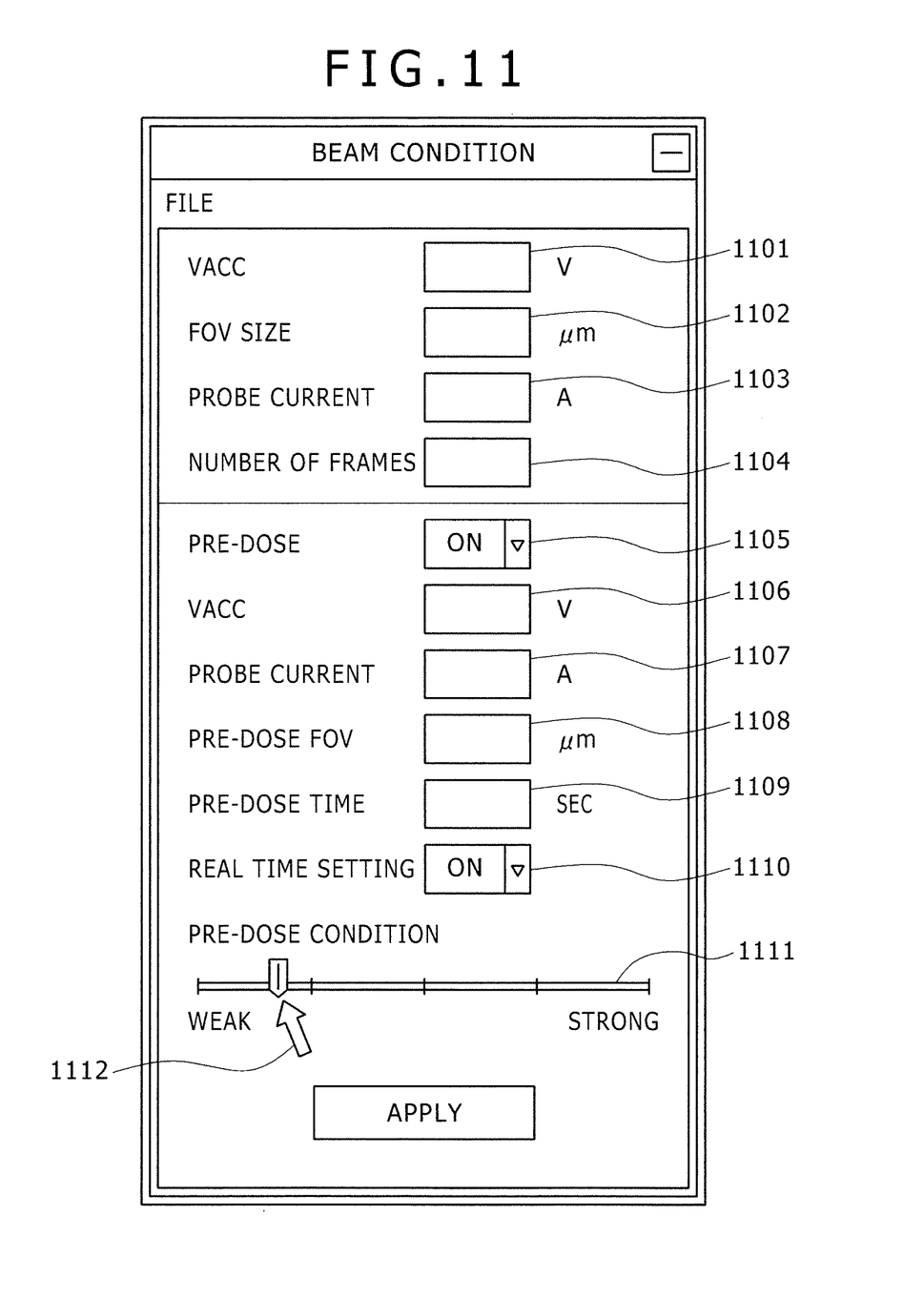
FIG. 11 is a diagram illustrating an example of a GUI screen for setting beam conditions for beam irradiation.

FIG. 11 is a diagram illustrating an example of a GUI screen for setting beam conditions for beam irradiation. The GUI screen exemplified in FIG. 11 appears, for instance, on the display device of the input device 909. In accordance with settings entered from the GUI screen, the optical condition setup section 905 sets the beam conditions and the signal computation section 907 determines the pre-dose stop timing. The GUI screen exemplified in FIG. 11 includes an acceleration voltage (Vacc) setup field 1101, a field-of-view (FOV) size setup field 1102, a beam current (probe current) setup field, and cumulative frame count setup field 1104. These setup fields are used to set the beam conditions for measurement.

The above-mentioned setup fields are beam setup fields for measurement. However, fields below the cumulative frame count setup field 1104 are used to set the pre-dose conditions. A pre-dose selection field 1105 is used to specify whether or not to perform pre-dosing. If "ON" is selected from this field, a beam scan is performed under beam conditions for charging the surface of a sample before beam irradiation is conducted under the conditions set by the fields 1101-1104.

An acceleration voltage setup field 1106, a beam current setup field 1107, and a pre-dose field-of-view size setup field 1108 are used to set the beam conditions for pre-dosing. These fields select beam conditions for charging the sample rather than beam conditions for measurement. For example, the acceleration voltage setup field 1106 selects an acceleration voltage that has a higher secondary electron emission efficiency than the acceleration voltage set by the acceleration voltage setup field 1101. The secondary electron emission efficiency with respect to the acceleration voltage varies with the type of sample. Therefore, it may be stored beforehand in the memory 904 and automatically read in accordance with the type of sample selected from a sample type selection field (not shown).

A pre-dose time setup field 1109 is used to set beam irradiation time for pre-dosing. The beam irradiation time for pre-dosing is set in accordance with a setting entered from this field. This field may be replaced by a field for setting a cumulative frame count. A charge is cumulatively stored in accordance with an increase in the pre-dose time. It is therefore preferred that the irradiation time be set to avoid the formation of an excessive charge and maximize the efficiency of raising secondary electrons from the bottom of a hole.

Meanwhile, the pre-dose irradiation time needs to be adjusted in such a manner as to suppress the occurrence of electrostatic breakdown and maximize the efficiency of raising secondary electrons from the bottom of a hole. For example, a charged state prevailing immediately before the occurrence of electrostatic breakdown is an optimal state for maximizing the efficiency of raising secondary electrons. However, such a state cannot readily be set only by adjusting the pre-dose irradiation time setting.

As such being the case, the GUI screen exemplified in FIG. 11 is provided with a pre-dose dynamic determination function setup field 1110 for setting the pre-dose stop timing by using an image derived from pre-dosing. This field can be set to either ON or OFF. When set to ON, this field prohibits the input of a value into the pre-dose time setup field 1109 or disables its setting and allows the pre-dose stop timing to be set in accordance with dynamic determination based on image analysis.

A scrollbar 1111 is provided with a pointer 1112. Moving the pointer 1112 as appropriate causes the scrollbar 1111 to adjust the intensity of pre-dosing within a range that does not cause electrostatic breakdown. More specifically, the pointer 1112 set to the maximum value of the scrollbar 1111 not only performs a process of stopping the pre-dosing when central noise is generated as indicated at (4) in FIG. 2 or when a predefined behavior is exhibited (before electrostatic breakdown) after the generation of the central noise, but also prohibits the selection of a higher intensity setting. This makes it possible to set desired pre-dose conditions within a range that does not cause electrostatic breakdown.

Further, image features chronologically appearing in an image at stages (1) to (4) in FIG. 2 are generated in accordance with the size of a charge. Therefore, when a pre-dose stop process based on extracted image features shown at stages (1) to (4) in FIG. 2 is performed in accordance with a pre-dose intensity selected by the scrollbar 1111, it is possible to select desired pre-dose conditions that prevail before the occurrence of electrostatic breakdown.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A charged particle radiation apparatus for acquiring signal waveform data or image data of a pattern formed on a sample in accordance with charged particles, the charged particles being obtained by scanning a charged particle beam emitted from a charged particle source, the charged particle radiation apparatus comprising:
    a control device that switches between a first charged particle beam and a second charged particle beam, the first charged particle beam being scanned to acquire the data, the second charged particle beam being scanned over the sample before the scan of the first charged particle beam and used to charge the sample more than the first charged particle beam;
    wherein the control device is configured to:
    acquire at least one of signal waveform data and image data about a pattern formed on the sample in accordance with a scan performed on the sample by the second charged particle beam; and
    stop, when the acquired data has proved to be indicative of a predetermined state, the scanning of the second charged particle beam or register, on a predetermined storage medium, the timing at which the acquired data has proved to be indicative of the predetermined state as a scan stop timing for the second charged particle beam.

2. The charged particle radiation apparatus according to claim 1,
    wherein the control device stores, in the storage medium, temporal changes in the amount of features, the amount of features being acquired in accordance with at least one of signal waveform data and image data which are derived from the scan of the first charged particle beam.

3. The charged particle radiation apparatus according to claim 2,
    wherein the control device includes a display device for displaying changes in the amount of features and stops the scan of the second charged particle beam in accordance with a setting selected from the display device.

4. The charged particle radiation apparatus according to claim 1,
    wherein the control device stops the scan of the second charged particle beam when the amount of changes in the amount of features, the amount of features being acquired in accordance with at least one of signal waveform data and image data which are derived from the scan of the first charged particle beam, has proved to be indicative of a predetermined state.

5. The charged particle radiation apparatus according to claim 1,
    wherein the control device scans the first charged particle beam over a region that is included in a region of the sample over which the second charged particle beam is scanned.

6. A charged particle radiation apparatus for acquiring signal waveform data or image data of a pattern formed on a sample in accordance with charged particles, the charged particles being obtained by scanning a charged particle beam emitted from a charged particle source, the charged particle radiation apparatus comprising:
    a control device that switches between a first charged particle beam and a second charged particle beam, the first charged particle beam being scanned to acquire the data, the second charged particle beam being scanned over the sample before the scan of the first charged particle beam and used to charge the sample more than the first charged particle beam;
    a display device that displays temporal changes in the amount of features extracted from at least one of signal waveform data and image data which are derived from the scan of the second charged particle beam; and
    an input device that sets a scan stop timing for the second charged particle beam.

* * * * *